United States Patent
Azzolina (10) Patent No.: US 7,585,322 B2
(45) Date of Patent: Sep. 8, 2009

(54) CARDIOCIRCULATORY AIDING DEVICE

(75) Inventor: Gaetano Azzolina, Licciana Nardi (IT)

(73) Assignee: ABM Heart Technologies, LLC, Lynwood, WA (US)

( * ) Notice: Subject to any disclaimer, the term of this patent is extended or adjusted under 35 U.S.C. 154(b) by 0 days.

(21) Appl. No.: 11/871,590

(22) Filed: Oct. 12, 2007

(65) Prior Publication Data
US 2008/0027536 A1    Jan. 31, 2008

Related U.S. Application Data (63) Continuation-in-part of application No. 11/188,450, filed on Jul. 25, 2005, now abandoned.

(30) Foreign Application Priority Data

Jul. 1, 2005    (IT)    ............... UD2005A0112

(51) Int. Cl.
*A61M 1/12*    (2006.01)

(52) U.S. Cl. .................. 623/3.21; 600/16; 600/18; 623/3.1; 623/3.16

(58) Field of Classification Search ........... 600/16, 600/18; 623/3.1, 3.2, 3.12, 3.16, 3.17, 3.21, 623/3.22, 3.26, 3.29
See application file for complete search history.

(56) References Cited

U.S. PATENT DOCUMENTS

| | | | | |
|---|---|---|---|---|
| 3,766,567 A | * | 10/1973 | Kahn et al. | 623/3.21 |
| 4,222,127 A | * | 9/1980 | Donachy et al. | 623/3.21 |
| 4,578,077 A | | 3/1986 | Joh | 623/3 |
| 4,581,029 A | | 4/1986 | Joh | 623/3 |
| 4,588,404 A | * | 5/1986 | Lapeyre | 623/3.21 |
| 4,846,831 A | * | 7/1989 | Skillin | 623/3.1 |
| 2004/0054251 A1 | | 3/2004 | Liotta | 600/17 |

\* cited by examiner

*Primary Examiner*—Carl H Layno
*Assistant Examiner*—Eugene T Wu
(74) *Attorney, Agent, or Firm*—St. Onge Steward Johnston & Reens LLC (57) ABSTRACT

A cardiocirculatory aiding device is disclosed generally comprising a housing with a cavity, an inlet, an outlet, and first and second sides with apertures therein, first and second shells mounted to the sides of the housing, and first and second membranes disposed between the housing and the shells such that the membranes cover the apertures in the sides of the housing, thereby creating a central blood chamber and two outer gas chambers. A pump supplies gas through a duct into the gas chambers to cause the membranes to flex into the blood chamber to pump the blood in that chamber through the outlet. In some embodiments, the pump is external and the duct passes through an incision in the body. In some embodiments, the membranes are elastomer membranes.

24 Claims, 5 Drawing Sheets

CARDIOCIRCULATORY AIDING DEVICE

CROSS-REFERENCE TO RELATED APPLICATIONS

This application is a continuation-in-part of U.S. patent application Ser. No. 11/188,450, filed Jul. 25, 2005, now abandoned which claims priority to Italian Patent Application No. UD2005A000112, filed on Jul. 1, 2005, the contents of each of which are hereby incorporated herein by reference in their entirety.

FIELD OF THE INVENTION

The present invention relates to an apparatus and method for aiding cardiac circulation. More specifically, the invention relates to a device used in conjunction with a pump for expanding gas chambers adjacent a blood chamber to pump blood in and out of the blood chamber.

BACKGROUND OF THE INVENTION

Cardiocirculatory aiding devices are generally well known in the practice of cardiosurgery. These devices, which include various types of mechanical devices for aiding the functioning of the heart, are commonly referred to as a Ventricular Assist Device (V.A.D.) or Total Artificial Heart (T.A.H.). Such devices are able to mechanically pump the blood, thereby producing pulse or continuous hematic flows.

Such devices can be used to solve reversible acute cardiac insufficiencies (e.g.: infarct, myocarditis, morphological pathologies, postcardiotomy, etc.), or are used for supporting the circulatory function while one awaits a heart transplantation, or even indefinitely in situations of irreversible, chronically problematic pathologies (i.e., "Therapy destination").

Different ventricular aid devices have been present for many years, for both the left and the right, and for biventricular (T.A.H.). Some of them are commercially available, while others have been developed only on an experimental level. However, these existing designs suffer from a number of drawbacks.

In most cases, the existing devices have some difficulties in terms of positioning the device inside the chest, due primarily to dimension and weight problems, as well as in the application modalities. Other common drawbacks result from their internal geometries and their pumping modalities, which will sometimes cause hemolysis or the formation of coagulations.

A significant negative aspect of the known devices is their undesirable weight and the encumbrance of the operating unit, particularly with respect to the pumping device, which generally limits or precludes the portability of the entire device. More significantly, however, is that existing devices are simply too large for certain individuals. Today, a ten pound child experiencing heart failure has little or no hope. However, if a small enough device could be employed, it could be implanted into a small child, giving his or her heart a chance to heal and grow, after which the device could then be removed. Similarly, a one hundred pound woman experiences the same size and installation problems associated with the existing devices and would likewise benefit from a smaller device than is currently available.

An additional problem created by the current devices is that they include complex internal mechanisms and, given this complexity, they are not completely reliable. In fact, it is known that, the more complex an apparatus is, the greater the likelihood the device will experience jamming, which, of course, is very dangerous. When the device jams or stops, it is unlikely the individual will be able to obtain immediate medical assistance to intervene, and thus, such incidents will often prove fatal.

Moreover, this complexity adds other dangers, as such devices will typically incorporate an electrical and/or electromagnetic apparatus, with all the obvious potential dangers accompanying such, while some devices require that separate parts be housed in different positions of the body, resulting in other surgical complications, undesirable encumbrances, and the danger of infection.

What is desired, therefore, is a device that efficiently, reliably, and safely pumps blood to assist the heart. What is further desired is a device that can be used in small areas. What is also desired is a device that is as mechanically uncomplicated as possible.

SUMMARY OF THE INVENTION

Accordingly, it is an object of the present invention to provide a cardiocirculatory aiding device with reduced encumbrance and weight.

It is a further object of the present invention to provide a cardiocirculatory aiding device that can be used in pediatric cases.

It is yet another object of the present invention to provide a cardiocirculatory aiding device with improved functionality, performance, and reliability.

It is still another object of the present invention to provide a cardiocirculatory aiding device that does not require any electric part to be installed inside of the human body.

It is yet another object of the present invention to provide a cardiocirculatory aiding device that that is easy to adjust and that enables one to intervene in the case of an emergency from outside the human body without the necessity of a complex apparatus.

In order to overcome the deficiencies of the prior art and to achieve at least some of the objects and advantages listed, the invention comprises a cardiocirculatory aiding device, including a housing having a cavity therein, a first side with a first aperture, and a second side with second aperture, first and second shells mounted to the first and second sides of the housing, respectively, the first and second shells each having a concave inner surface, a first membrane disposed between the first shell and the first side of the housing such that the first membrane covers the first aperture, the first membrane and the concave inner surface of the first shell at least partially defining a first gas chamber, a second membrane disposed between the second shell and the second side of the housing such that the second membrane covers the second aperture, the second membrane and the concave inner surface of the second shell at least partially defining a second gas chamber, wherein the housing and the first and second membranes at least partially define a blood chamber, an inlet and an outlet that communicate blood into and out of the blood chamber, a gas duct in fluid communication with the first and second gas chambers, and a pump connected to the gas duct, wherein the pump communicates gas into the first and second gas chambers via the gas duct that causes the first and second membranes to flex into the blood chamber and pump blood in the blood chamber through the outlet.

In some of these embodiments, the first and second shells are mounted to the first and second sides of the housing via a plurality of fasteners arranged along the perimeters of the shells. In certain embodiments, the inner surfaces of the shells are substantially spherical.

In certain embodiments, the first and second membranes comprise elastomer membranes. In some of these embodiments, the elastomer membranes comprise a silicon elastomer.

In some embodiments, the housing comprises polyoxymethylene.

In certain embodiments, the device further includes unidirectional valves for controlling flow through the inlet and outlet. In some cases, the device has only one inlet through which blood enters the blood chamber and only one outlet through which blood exits the blood chamber, and in some embodiments, the device includes a haemocompatible duct connected to the inlet for connecting the housing to an atrium.

In some embodiments, the housing has a top end and a bottom end, the inlet and the outlet are located at the top end of the housing, and the gas duct is connected to the housing at the bottom end of the housing. In certain of these embodiments, the first and second sides of the housing are substantially flat and have a generally bulbous profile, such that the width of each of the first and second sides gradually decreases at the bottom end of the housing. In some of the embodiments, the housing has a width the gradually decreases towards the bottom end of the housing.

In certain embodiments, the pump comprises an electropneumatic unit that produces a pulsed gas supply. In some of these embodiments, the frequency of the pulsed gas supply is variable. In some of these cases, the frequency of the pulsed gas supply is variable both manually and automatically. In certain embodiments, the pump comprises a flexible manual pump.

In some embodiments, the gas duct has a length sufficient to connect the pump to the housing when the housing is positioned inside a human body and the gas pumping device is positioned outside the human body. In certain embodiments, the duct comprises a flexible plastic material.

In another embodiment, the invention comprises a method of aiding cardiac circulation, the method including providing a housing having a cavity therein, a first side with a first aperture, a second side with second aperture, and inlet for communicating blood into the cavity, and an outlet for communicating blood out of the cavity, positioning a first membrane against the first side of the housing such that the first membrane covers the first aperture and positioning a second membrane against the second side of the housing such that the second membrane covers the second aperture, such that the housing and the first and second membranes at least partially define a blood chamber, mounting a first shell having a concave inner surface to the first side of the housing such that the first membrane and the concave inner surface of the first shell at least partially define a first gas chamber, mounting a second shell having a concave inner surface to the second side of the housing such that the second membrane and the concave inner surface of the second shell at least partially define a second gas chamber, connecting a first end of the gas duct to the housing such that the duct is in fluid communication with the first and second gas chambers, and connecting a second end of the gas duct to the pump, and using the pump to communicate gas into the first and second gas chambers via the gas duct to cause the first and second membranes to flex into the blood chamber and pump blood in the blood chamber through the outlet.

In some of these embodiments, the method further includes positioning the housing in a human body and positioning the pump outside of the human body. In some of these cases, the method further includes connecting the inlet of the housing to an atrium.

In some embodiments, the method includes controlling the volume flow of the blood pumped through the outlet by controlling the frequency at which the pump supplies the gas to the first and second gas chambers. In some embodiments, the method includes controlling the volume flow of the blood pumped through the outlet by controlling the amount of gas supplied to the first and second gas chambers by the pump.

DETAILED DESCRIPTION OF THE INVENTION

Figure 1:
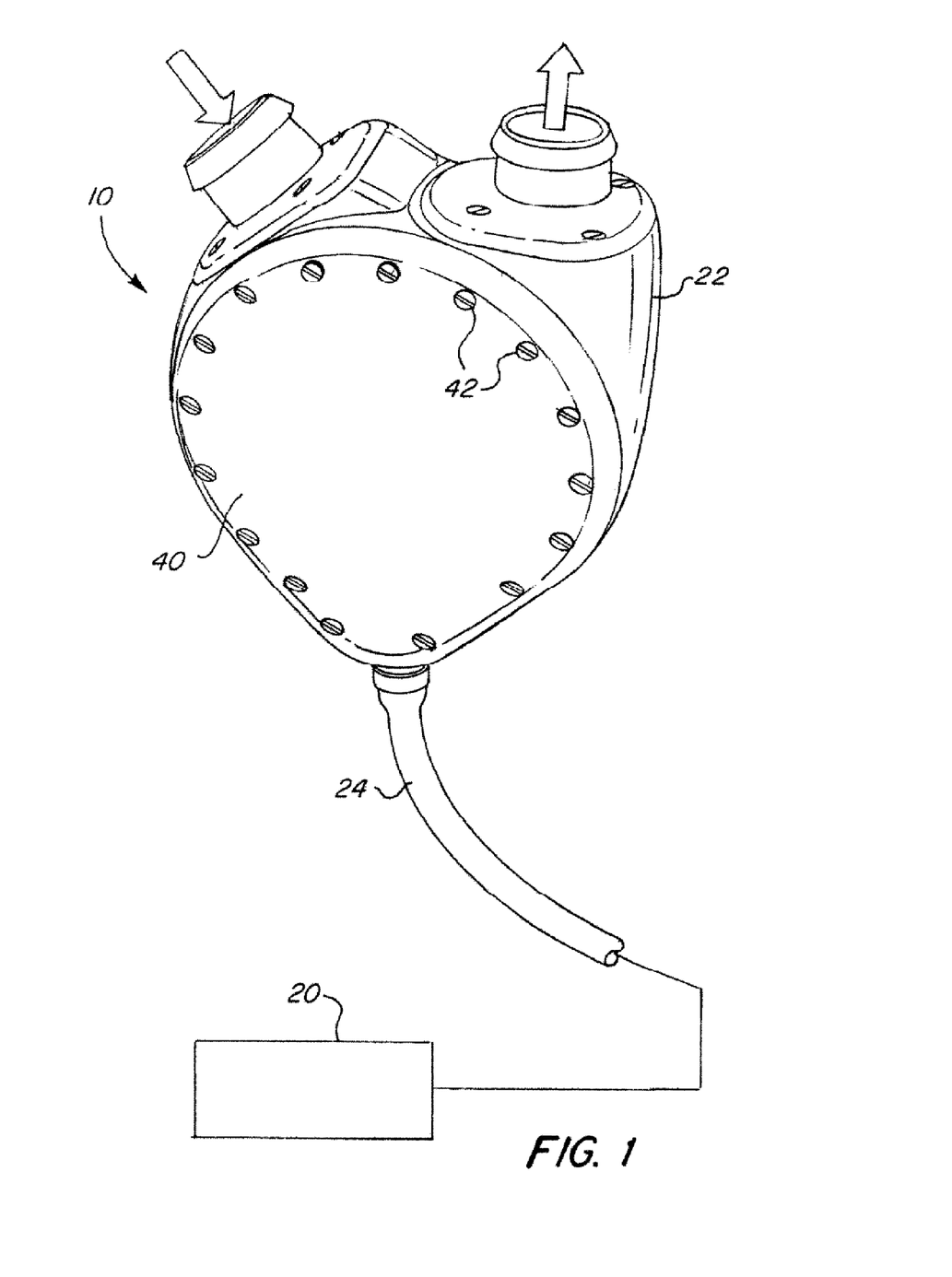
FIG. 1 is a perspective view of a cardiocirculatory aiding device in accordance with the invention.

The basic components of one embodiment of a cardiocirculatory aiding device 10 in accordance with the invention are illustrated in FIG. 1. The device 10 includes a pump 20 that supplies a gas, such as ambient air or oxygen, to a blood pumping device 22 via a duct 24. As will be explained in further detail below, the blood pumping device 22 is implanted in the body, while the gas pump 20 is positioned outside of the body. Accordingly, the duct 24 may be made of any material suitable for efficiently and safely communicating gas through a small incision and into the body. Typically, the duct 24 comprises a flexible plastic tube, though any flexible material that is both strong and light may be used, provided the chosen material does not irritate the body and is not prone to kinking. In certain advantageous embodiments, the tube 24 has an internal diameter of approximately 3.5 to 4 mm and an external diameter of approximately 5 to 6 mm.

Figure 2:
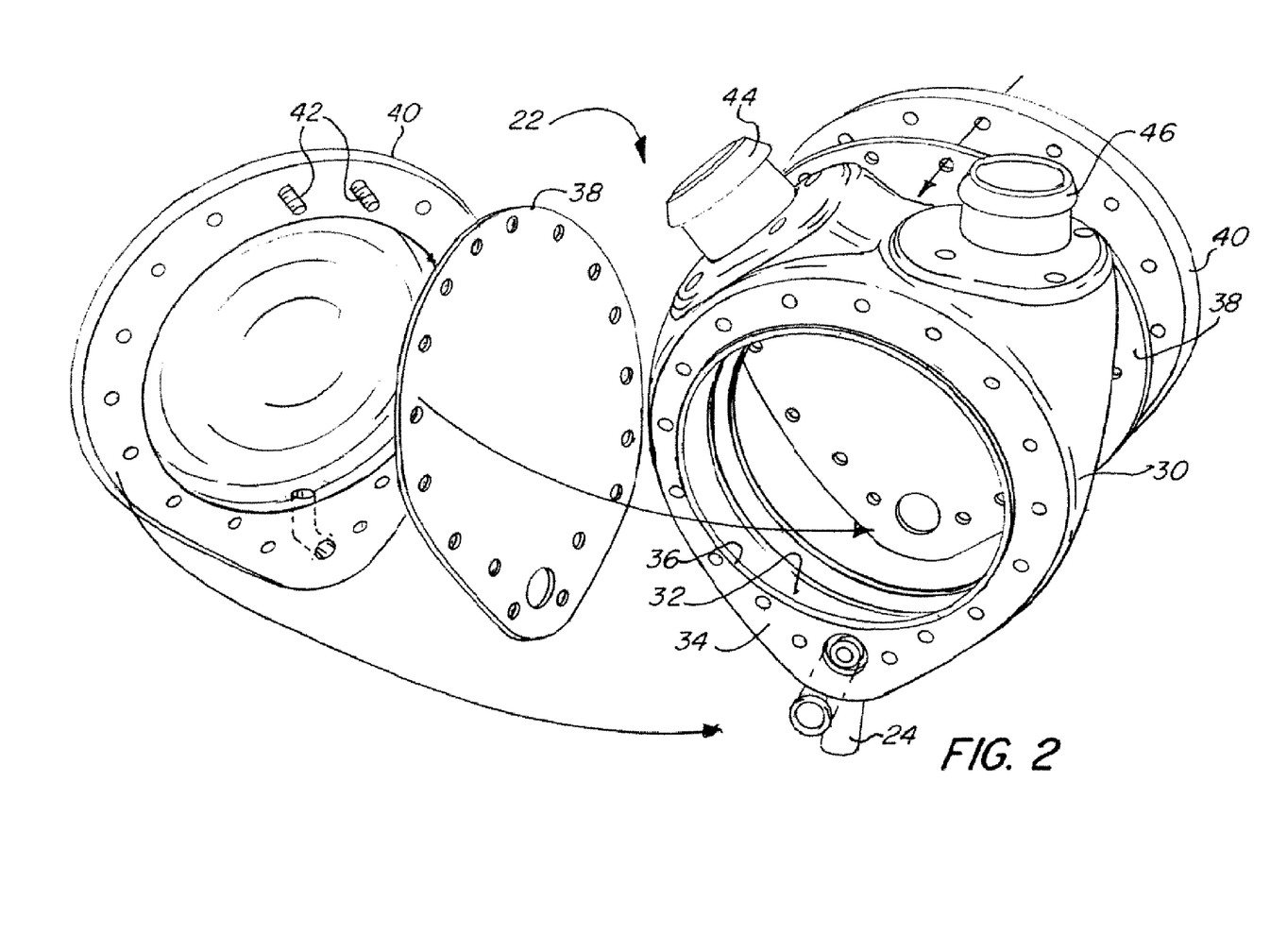
FIG. 2 is an exploded, perspective view of the blood pumping device of the cardiocirculatory aiding device of FIG. 1.

As shown more clearly in FIG. 2, the blood pumping device 22 includes a core housing 30 with a cavity 32 therein. In certain advantageous embodiments, the housing is made from Delrin (polyoxymethylene), though any lightweight material that is both rigid and safe may be employed, such as, for example, Dacron (polyethylene terephthalate), a carbon plastic material (e.g., pyrocarbon), metallic materials (e.g., titanium), or any other appropriate material.

The housing 30 has first and second sides 34, each of which has a large aperture 36 therein. An elastic membrane 38 is disposed over the aperture 36 on each side 34 of the housing 30, such that the membrane 38 covers the aperture 36. In certain advantageous embodiments, the membrane 38 comprises an elastomer, such as silicon rubber.

A rigid outer shell 40 is mounted to the central core housing 30, compressing the membrane 38 therebetween. Each of the shells 40 has a concave inner surface 41, which, in certain advantageous embodiments, is spherical. In some cases, the shell 40 is mounted to the housing 30 via a plurality of fasteners, such as miniature screws 42, along the perimeter of the shell 40 in order to produce a tight, secure compression of the membrane 38 against both the housing 30 and the shell 40.

The housing 30, as well as the membranes 38 and shells 40 mounted thereto, have a generally bulbous profile (as best shown in FIG. 1), such that the width of each of the first and second sides gradually decreases at the bottom end of said housing. Similarly, the width of the housing 30 gradually decreases towards the bottom (as best shown in FIGS. 3-4).

This results in an internal geometry of the cavity 32 that is hydrodynamic in such a way that stagnate zones of the blood are avoided, which otherwise could result in thrombogenesis and hemolysis.

Additionally, the housing 30 has an inlet 44 and an outlet 46, through which the blood enters and exits the cavity 32 of the core housing 30, as is further explained below. The direction of flow through the inlet 44 and outlet 46 is controlled by unidirectional valves, thereby ensuring that blood only flows through each valve in the appropriate direction. Such valves may be placed in the inlet 44 and outlet 46, or alternatively, in the connecting hoses that connect the inlet 44 and outlet 46 to the relevant portions of the cardiocirculatory system in order to reduce any noise or clicking sound produced by the valves.

Figure 3:
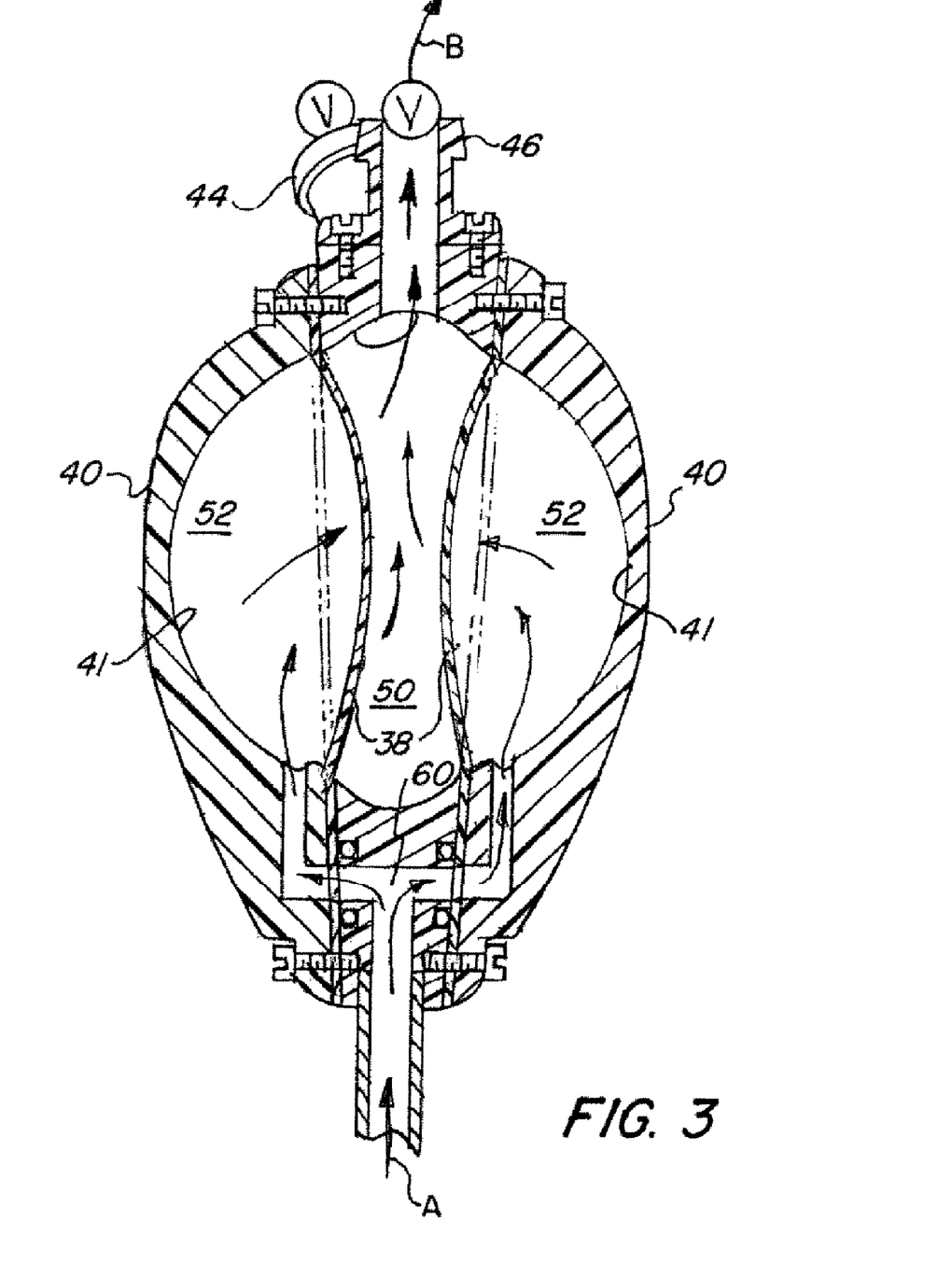
FIG. 3 is a cross-sectional view of the blood pumping device of FIG. 2 as blood is being discharged from the device.
Figure 4:
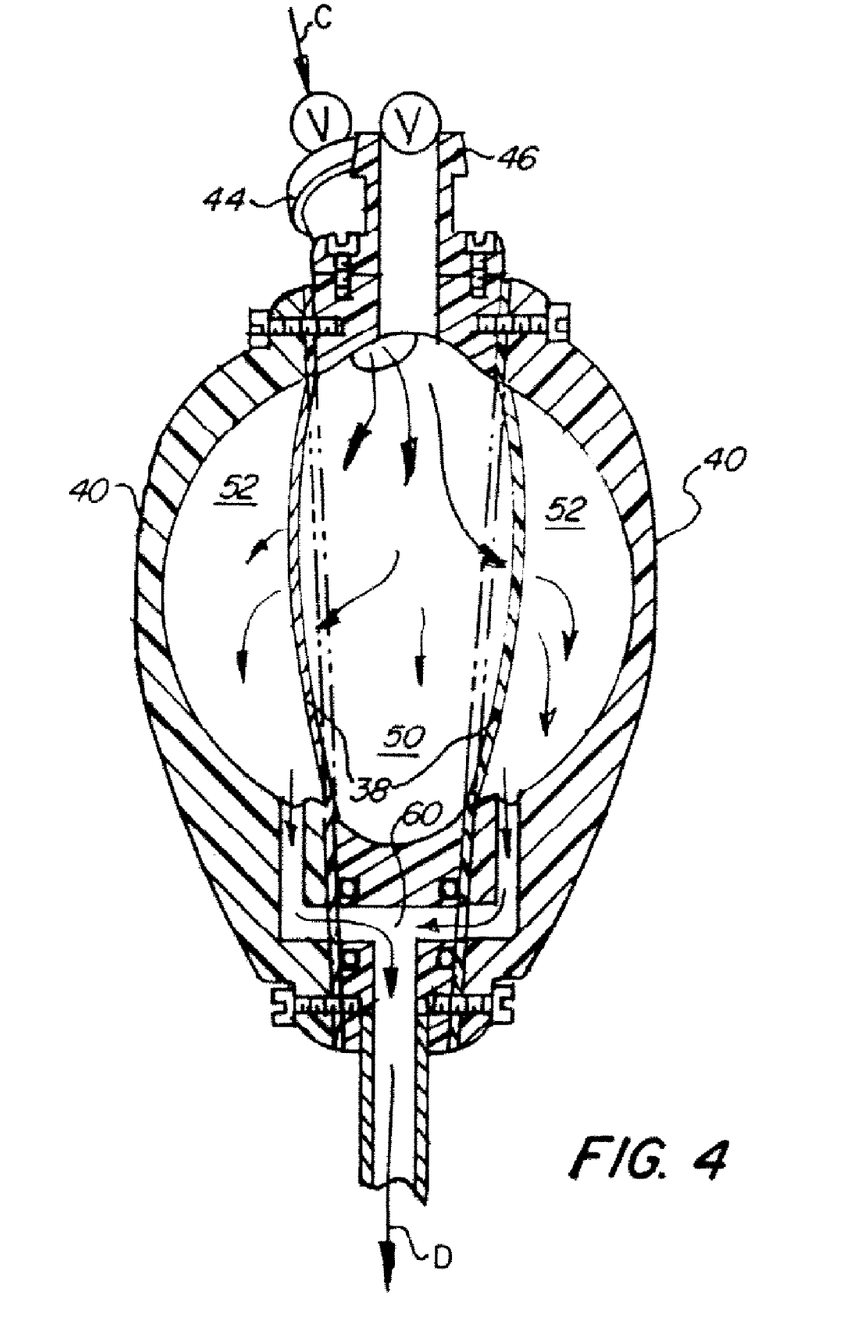
FIG. 4 is a cross-sectional view of the blood pumping device of FIG. 2 as blood is being drawn into the device.

As shown more clearly in FIG. 3, by clamping the membranes 38 against the housing 30 with the shells 40 as described above, a blood chamber 50 is formed by the housing 30 and the membranes 38. Additionally, on each side of the housing 30, a gas chamber 52 is formed by a membrane 38 and an outer shell 40.

The operation of the cardiocirculatory aiding device 10 is illustrated in FIGS. 3-4. The pump 20 pumps gas through the duct 24 to a gas passage 60 of the device 22, which directs the gas into the two gas chambers 52. (Indicated by arrows A). As the gas is pumped into the gas chambers 52, pressure is exerted on the membranes 38, causing them to flex into blood chamber 50. As the gas chambers 52 expand, the volume of the blood chamber 50 shrinks, urging the blood therein upwards and out through the outlet 46. (Indicated by arrows B). Approximately three quarters of the blood in the blood chamber 50 is discharged, leaving about one quarter of the blood to flow back into the chamber 50, thereby retaining a constant movement of blood therein so as not to permit any stagnation of the blood.

Subsequently, the gas is discharged from the gas chambers 52 back through the gas passage 60 (indicated by arrows D), releasing the pressure in the gas chambers 52 such that the membranes 38 move back in the other direction, thereby increasing the volume in the blood chamber 50 and drawing more blood through the inlet 44 (indicated by arrows C). If it is desired to create a vacuum for sucking blood through the inlet 44, the air can be drawn from the gas chambers 52 such that the membranes 38 actually recoil slightly into the gas chambers 52 rather than just returning to an unflexed position. However, it is important to note that the membranes 38 do not flex such that they would touch the inner surfaces 41 of the outer shells 40, which ensures that the membranes 38 avoid unnecessary wear. By repeating this supply and discharge of gas to and from the gas chambers 52, blood is continually pumped in and out of the blood chamber 50 as the flexing membranes 38 repeatedly cause the blood chamber to increase and decrease in size. By generating this pumping effect by supplying gas into the concave cavities of the opposing outer shells 40, pressure is able to be uniformly applied to the blood chamber 50. In this way, a proper pulsing hematic flow can be achieved.

Significantly, by employing this method for pumping the blood in and out of the device, one is able to precisely control the blood flow by altering the frequency and or pressure at which the gas is supplied. For example, the speed of the pumping can be altered by changing the frequency at which the gas is received by and discharged from the gas chambers 52, thereby altering the frequency at which the membranes 38 flex or 'pulse' into the blood chamber 50. Similarly, the volume of blood discharged from the blood chamber 50 can be increased by simply increasing the amount of gas that the pump 20 supplies to the gas chambers 52, thereby increasing the pressure that is applied to the membranes 38, causing them to flex further into the blood chamber 50 and push more blood through the outlet 46.

Figure 5:
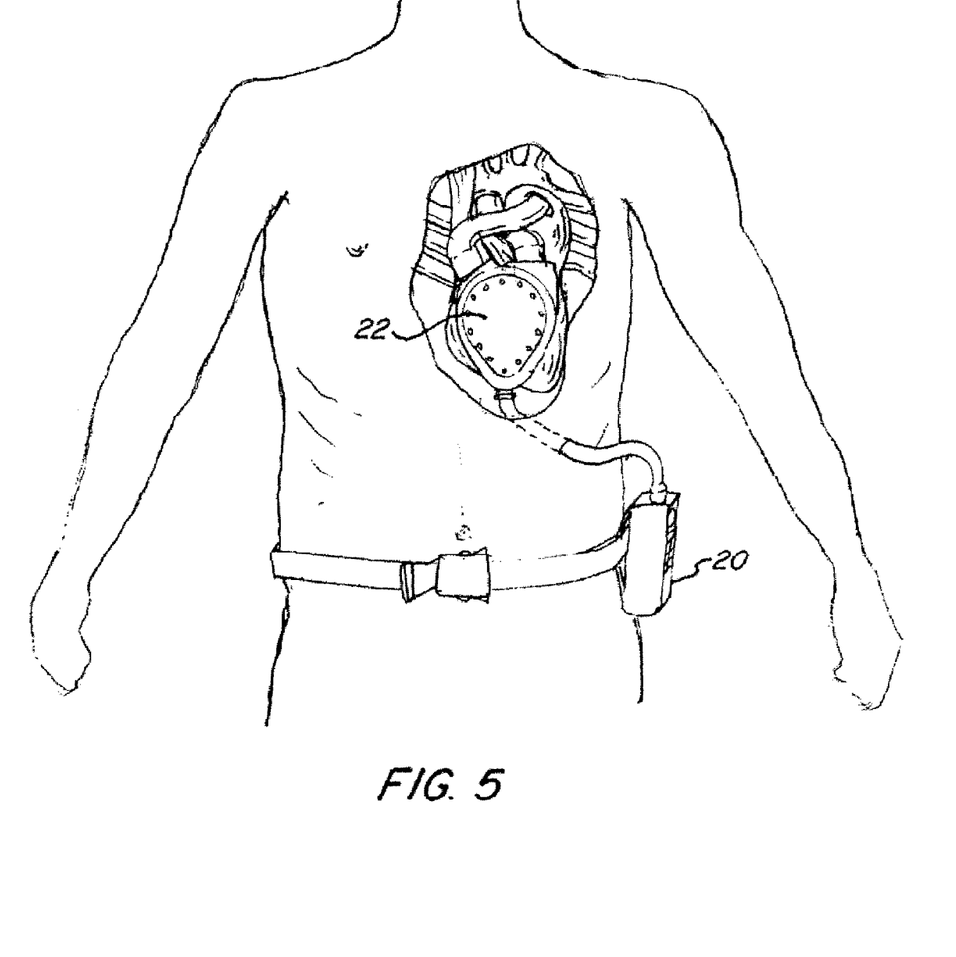
FIG. 5 is a perspective view of the cardiocirculatory aiding device of FIG. 1 implanted in a human body.

As shown in FIG. 5, the blood pumping device 22 is implanted in the body in order to assist the pumping of the heart. Typically, the inlet 44 of the blood pumping device 22 is placed in fluid communication with the left atrium of the heart via a haemocompatible duct, such that the blood chamber 50 can receive blood therefrom. However, when necessary, a connecting hose may be sewn directly to the left ventricle itself. The outlet 46 is placed in fluid communication with the aorta so that when the blood exits the blood chamber 50 (as further described below), the blood is discharged directly into the aorta. In this way, the left ventricle is effectively bypassed. In instances where it is desired to bypass the right ventricle, the inlet 44 is placed in fluid communication with the right atrium, and the outlet 46 is placed in fluid communication with the pulmonary artery.

The pump 20, on the other hand, is positioned outside the body and pumps the gas through the tube 24, which passes through an aseptic transcutaneous opening in the body. In this way, a patient can be attached to pump as the situation requires, such as, for example, a portable pump in an ambulance, or, where prolonged use is desired, a small pump attached to one's belt. Accordingly, the motor and electronic components of such a device are all located outside the person's body, such that it is easily adjustable as the user's condition changes, is easily accessible for maintenance/replacement, and most importantly, removes any dangers of electric shock.

In fact, if the pump 20 were to fail, the user could quickly replace the pump 20 with a small manual one so that the user could hand pump the blood until emergency assistance arrives. Accordingly, the external pump 20 may be of any type, including both hand pumps and electro-pneumatic units, which can be powered by a battery and/or accumulators. Such pumps may be of any variety, such as piston, diaphragm, etc.

The beat-frequency imposed to the device could be between 90-180 pulses/min., and may be variable, both manually and automatically by a regulating system within the gas pump 20. In certain advantageous embodiments, this frequency is asynchronous with the natural beat frequency of the heart. By providing high-frequency asynchronous pulses, which does not conflict with the object of achieving correct hematic perfusion, a very small size and weight for the device 22 can be employed.

As a result of the aforementioned arrangement, a cardiocirculatory aiding device can be made small to fit into a ten pound child (e.g., 50-60 grams in device weight) or much larger for a five hundred pound individual (e.g., 150 grams in device weight). The device is very light in weight and very easy to manufacture in small, medium or larger sizes. A particular device size and control of the particular output flow needed (which is controlled by the chamber size, frequency, and pressure imparted on the membrane) can be used as appropriate for the particular patient's size and weight. Accordingly, the above-described design provides a versatile, safe, and extremely efficient life-saving device with various applications, including bridge to transplant, destination therapy (as an alternative to heart transplantation), and explantation.

The advantages of the aforementioned design cannot be understated. By using this blood pumping design, there is no centrifugation, pushing, twisting, or shaking of the blood (it is not an axial or centrifugal flow pump, and there is no propeller, magnets, rotors, or shakers), which allows a more natural blood flow that causes no damage to the blood cells. The device can be manufactured at about 50-60 grams, which is much less than the existing devices currently being used, which average about 300-400 grams, making this the first cardiocirculatory aiding device truly suitable for children. It allows for minimally invasive surgery—standard surgery with only a small incision on the side of the chest—as opposed to the open heart surgery needed with all other known heart devices, thereby causing less trauma to patients and significantly reducing medical, hospital, and insurance costs. Finally, this device allows a complete bypass of the ventricle, thereby significantly reducing surgery time and complexity (e.g., about 2.5 hours, compared to 6-8 hours for existing surgeries) and allowing the ventricle and heart to recover more quickly. No other known device does this.

It should be noted that, while use of the above-described device is substantially directed to assisting the heart, it can also be used to replace it in extremis by using two such devices (i.e., right and left). It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A method of aiding cardiac circulation, the method comprising:
   providing a housing having a cavity therein, a first sidewall with an outer surface, a first hole passing through the first sidewall into the cavity, a second sidewall with an outer surface, a second hole passing through the second sidewall into the cavity, an inlet for communicating blood into the cavity, and an outlet for communicating blood out of the cavity;
   positioning a first membrane against the outer surface of the first sidewall of the housing such that the first membrane covers the first hole, the first membrane being substantially flat in an unflexed position, and positioning a second membrane against the outer surface of the second sidewall of the housing such that the second membrane covers the second hole, the second membrane being substantially flat in an unflexed position, such that the housing and the first and second membranes at least partially define a blood chamber;
   mounting a first shell having a concave inner surface to the outer surface of the first sidewall of the housing such that the first membrane and the concave inner surface of the first shell at least partially define a first gas chamber;
   mounting a second shell having a concave inner surface to the outer surface of the second sidewall of the housing such that the second membrane and the concave inner surface of the second shell at least partially define a second gas chamber;
   connecting a first end of the gas duct to the housing such that the duct is in fluid communication with said first and second gas chambers; and
   connecting a second end of the gas duct to a pump; and
   using the pump to communicate gas into the first and second gas chambers via said gas duct to cause said first and second membranes to flex through said first and second holes, respectively, and into the blood chamber and pump blood in the blood chamber through the outlet.

2. The method of claim 1, further comprising positioning the housing in a human body and positioning the pump outside of the human body.

3. The method of claim 2, further comprising connecting the inlet of the housing to an atrium.

4. The method of claim 1, further comprising controlling the volume flow of the blood pumped through the outlet by controlling the frequency at which the pump supplies the gas to the first and second gas chambers.

5. The method of claim 1, further comprising controlling the volume flow of the blood pumped through the outlet by controlling the amount of gas supplied to the first and second gas chambers by the pump.

6. The method of claim 1, wherein said first and second membranes comprise elastomer membranes.

7. A cardiocirculatory aiding device, comprising:
   a housing having a generally bulbous profile, a substantially flat first sidewall with a hole passing therethrough and having an outer surface, and a substantially flat second sidewall with a hole passing therethrough and having an outer surface;
   a first shell with a concave inner surface mounted to the outer surface of the first sidewall of said housing;
   a second shell with a concave inner surface mounted to the outer surface of the second sidewall of said housing;
   a first membrane sandwiched between said first shell and the outer surface of the first sidewall of said housing such that said first membrane covers said first hole, said first membrane comprising an elastomer sheet having inner and outer side surfaces that is substantially flat in an unflexed position;
   a second membrane sandwiched between said second shell and the outer surface of the second sidewall of said housing such that said second membrane covers said second hole, said second membrane comprising an elastomer sheet having inner and outer side surfaces that is substantially flat in an unflexed position;
   wherein the first shell is mounted to the outer surface of the first sidewall of said housing via a first plurality of fasteners passing through the perimeter of said first shell, through the perimeter of said first membrane, and into the outer surface of the first sidewall of said housing, and the second shell is mounted to the outer surface of the second sidewall of said housing via a second plurality of fasteners passing through the perimeter of said second shell, through the perimeter of said second membrane, and into the outer surface of the second sidewall of said housing;
   wherein an inner surface of said housing and the inner side surfaces of said first and second membranes define a blood chamber, the outer side surface of said first membrane and the concave inner surface of said first shell define a first gas chamber, and the outer side surface of said second membrane and the concave inner surface of said second shell at least partially define a second gas chamber;
   an inlet and an outlet that communicate blood into and out of the blood chamber;
   a gas duct in fluid communication with said first and second gas chambers; and
   a pump connected to said gas duct, wherein said pump communicates gas into said first and second gas chambers via said gas duct that causes said first and second membranes to flex through said first and second holes, respectively, and into said blood chamber to pump blood in the blood chamber through said outlet.

8. A cardiocirculatory aiding device, comprising:
   a housing having a cavity therein, a first sidewall with an outer surface, a first hole passing through the first sidewall into the cavity, a second sidewall with an outer surface, and a second hole passing through the second sidewall into the cavity;

first and second shells mounted to the outer surfaces of the first and second sidewalls of said housing, respectively, said first and second shells each having a concave inner surface;

a first membrane sandwiched between said first shell and the outer surface of the first sidewall of said housing such that said first membrane covers said first hole, said first membrane being substantially flat in an unflexed position, said first membrane and the concave inner surface of said first shell at least partially defining a first gas chamber;

a second membrane sandwiched between said second shell and the outer surface of the second sidewall of said housing such that said second membrane covers said second hole, said second membrane being substantially flat in an unflexed position, said second membrane and the concave inner surface of said second shell at least partially defining a second gas chamber;

wherein said housing and said first and second membranes at least partially define a blood chamber;

an inlet and an outlet that communicate blood into and out of the blood chamber;

a gas duct in fluid communication with said first and second gas chambers; and a pump connected to said gas duct, wherein said pump communicates gas into said first and second gas chambers via said gas duct that causes said first and second membranes to flex through said first and second holes, respectively, and into said blood chamber and pump blood in the blood chamber through said outlet.

9. The device of claim 8, further comprising unidirectional valves for controlling flow through said inlet and said outlet.

10. The device of claim 9, wherein:
said housing has a top end and a bottom end;
said inlet and said outlet are located at the top end of said housing; and
said gas duct is connected to said housing at the bottom end of said housing.

11. The device of claim 10, wherein each of the first and second sidewalls of said housing are substantially flat and have a generally bulbous profile, such that the width of each of the first and second sidewalls gradually decreases at the bottom end of said housing.

12. The device of claim 10, wherein said housing has a width that gradually decreases towards the bottom end of said housing.

13. The device of claim 8, wherein said pump comprises an electro-pneumatic unit that produces a pulsed gas supply.

14. The device of claim 13, wherein the frequency of said pulsed gas supply is variable.

15. The device of claim 14, wherein the frequency of said pulsed gas supply is variable both manually and automatically.

16. The device of claim 8, wherein said first and second membranes comprise elastomer membranes.

17. The device of claim 16, wherein said elastomer membranes comprise a silicon elastomer.

18. The device of claim 8, wherein said first and second shells are mounted to the first and second sidewalls of said housing via a plurality of fasteners arranged along the perimeters of said shells.

19. The device of claim 8, wherein the inner concave surfaces of said first and second shells are substantially spherical.

20. The device of claim 8, wherein said housing comprises polyoxymethylene.

21. The device of claim 8, wherein said device has only one inlet through which blood enters said blood chamber and only one outlet through which blood exits said blood chamber.

22. The device of claim 8, further comprising a haemocompatible duct connected to said inlet for connecting said housing to an atrium.

23. The device of claim 8, wherein said pump comprises a flexible manual pump.

24. The device of claim 8, wherein said duct comprises a flexible plastic material.

* * * * *